(12) United States Patent
Van Der Borght et al.

(10) Patent No.: US 11,540,062 B2
(45) Date of Patent: Dec. 27, 2022

(54) HEARING PROSTHESIS SYSTEM HAVING INTERCHANGEABLE HOUSINGS

(71) Applicant: Cochlear Limited, Macquarie University (AU)

(72) Inventors: Gunther Van Der Borght, Wahroonga (AU); Jan Janssen, St. Ives (AU)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 17/672,284

(22) Filed: Feb. 15, 2022

(65) Prior Publication Data

US 2022/0174429 A1 Jun. 2, 2022

Related U.S. Application Data

(63) Continuation of application No. 17/157,297, filed on Jan. 25, 2021, which is a continuation of application
(Continued)

(30) Foreign Application Priority Data

Dec. 22, 2003 (AU) .............................. 2003907101

(51) Int. Cl.
*A61N 1/00* (2006.01)
*H04R 25/00* (2006.01)
(Continued)

(52) U.S. Cl.
CPC ......... *H04R 25/43* (2013.01); *A61N 1/36038* (2017.08); *A61N 1/37247* (2013.01);
(Continued)

(58) Field of Classification Search
CPC .................... A61N 1/36038; A61N 1/37247
See application file for complete search history.

(56) References Cited

U.S. PATENT DOCUMENTS 4,890,330 A 12/1989 Meyer
4,918,737 A 4/1990 Luethi
(Continued)

FOREIGN PATENT DOCUMENTS

DE        3723809 A1    1/1989
DE        10228828 C1  10/2003
WO     2005062668 A1   7/2005

OTHER PUBLICATIONS

International Search Report and Written Opinion for PCT/AU2004/001803, dated Mar. 30, 2005.
(Continued)

*Primary Examiner* — Scott M. Getzow
(74) *Attorney, Agent, or Firm* — Pilloff Passino & Cosenza LLP; Martin J. Cosenza

(57) ABSTRACT

A system, including a first housing containing a speech processor that receives signals output by a microphone of the hearing prosthesis, a second housing removably connectable to the first housing at a bottom of the first housing, the bottom being at a first end of the first housing that is a wider end relative to a second end of the first housing opposite the first end and a first device removably connectable to the first housing when the second housing is disconnected from the first housing, wherein the first housing is part of a behind-the-ear (BTE) device, the second housing is part of a second device, and the system is a cochlear implant hearing prosthesis system.

30 Claims, 5 Drawing Sheets

Related U.S. Application Data

No. 16/031,515, filed on Jul. 10, 2018, now Pat. No. 10,904,675, which is a continuation of application No. 15/188,040, filed on Jun. 21, 2016, now Pat. No. 10,029,095, which is a continuation of application No. 14/337,540, filed on Jul. 22, 2014, now Pat. No. 9,375,572, which is a continuation of application No. 10/582,240, filed as application No. PCT/AU2004/001803 on Dec. 22, 2004, now Pat. No. 8,788,050.

(51) Int. Cl.
*A61N 1/36* (2006.01)
*A61N 1/372* (2006.01)

(52) U.S. Cl.
CPC .......... *H04R 25/556* (2013.01); *H04R 25/65* (2013.01); *H04R 25/554* (2013.01); *H04R 25/558* (2013.01); *H04R 2225/021* (2013.01); *H04R 2225/43* (2013.01); *H04R 2225/51* (2013.01); *H04R 2225/67* (2013.01)

(56) References Cited

U.S. PATENT DOCUMENTS

| | | |
|---|---|---|
| 5,204,917 A | 4/1993 | Arndt et al. |
| 5,802,183 A | 9/1998 | Scheller et al. |
| 5,824,022 A | 10/1998 | Zilberman et al. |
| 6,157,728 A | 12/2000 | Tong et al. |
| 6,532,295 B1 | 3/2003 | Brimhall et al. |
| 6,546,110 B1 | 4/2003 | Vonlanthen |
| 6,731,770 B1 | 5/2004 | Vonlanthen |
| 6,748,094 B1 | 6/2004 | Tzviskos et al. |
| 7,020,298 B1 | 3/2006 | Tzviskos et al. |
| 7,110,822 B1 | 9/2006 | Palmer |
| 7,142,926 B2 | 11/2006 | Crawford |
| 7,157,808 B2 | 1/2007 | Seligman |
| 7,349,741 B2 | 3/2008 | Maltan et al. |
| 7,519,194 B2 | 4/2009 | Niederdrank et al. |
| 7,561,920 B2 | 7/2009 | Faltys et al. |
| 7,638,898 B2 | 12/2009 | Peter |
| 7,818,066 B1 | 10/2010 | Palmer |
| 8,155,746 B2 | 4/2012 | Maltan et al. |
| 8,175,310 B2 | 5/2012 | Nielsen et al. |
| 10,904,675 B2 | 1/2021 | Van Der Borght et al. |
| 2004/0052388 A1 | 3/2004 | Niederdrank |
| 2005/0075149 A1 | 4/2005 | Gerber et al. |
| 2007/0282394 A1 | 12/2007 | Segel et al. |
| 2008/0288022 A1 | 11/2008 | Van der Borght et al. |
| 2021/0219064 A1 | 7/2021 | Van Der Borght et al. |

OTHER PUBLICATIONS

English Translation of Office Action for Austria Patent Application No. A9441/2004, dated May 6, 2009.
English Translation of Office Action for Austria Patent Application No. A9441/2004, dated Dec. 16, 2009.
Office Action for Korea Patent Application No. 10-2006-7013652, dated May 12, 2011.
Office Action for Korea Patent Application No. 10-2006-7013652, dated Mar. 22, 2012.

HEARING PROSTHESIS SYSTEM HAVING INTERCHANGEABLE HOUSINGS

CROSS-REFERENCE TO RELATED APPLICATIONS

The present application is a Continuation application of U.S. patent application Ser. No. 17/157,297, filed Jan. 25, 2021, which is a Continuation application of U.S. patent application Ser. No. 16/031,515, filed Jul. 10, 2018, now U.S. Pat. No. 10,904,675, which is a Continuation application of U.S. patent application Ser. No. 15/188,040, filed Jun. 21, 2016, now U.S. Pat. No. 10,029,095, which is a Continuation application of U.S. patent application Ser. No. 14/337,540, filed Jul. 22, 2014, now U.S. Pat. No. 9,375,572, which is a Continuation application of U.S. patent application Ser. No. 10/582,240, filed Aug. 4, 2008, now U.S. Pat. No. 8,788,050, which is a National Stage of PCT/AU2004/001803, filed Dec. 22, 2004, which claims priority to AU Application No. 2003907101, filed Dec. 22, 2003, the entire contents of these applications being hereby incorporated by reference herein in their entirety.

TECHNICAL FIELD

The disclosure relates to hearing prostheses and in particular, to external, wearable components of hearing prostheses.

BACKGROUND

A cochlear implant hearing prosthesis delivers electrical stimulation to the auditory nerve fibres thereby allowing the brain to perceive a hearing sensation resembling the natural hearing sensation normally delivered by the auditory nerve. Such systems have typically comprised an external component and an implantable internal component that cooperate together to provide the sound sensation to the recipient. The external component generally comprises a microphone for detecting sounds, such as speech and environmental sounds, a speech processor that converts the detected sounds, particularly speech, into a coded signal; a power source, such as a battery, and an external transmitter antenna. The coded signal is transmitted transcutaneously to the internal component. The internal component comprises a receiver antenna, a receiver/stimulator unit, and an intracochlear electrode assembly.

More specifically, as shown in prior art drawing FIG. 5, a cochlear implant hearing prothesis that comprises an external assembly of components 51 and an implantable assembly of components 52.

The external assembly 51 includes a primary signal processor unit in the form of a speech processor unit 56, a transmission coil 57 and a microphone unit 58. The primary signal processor unit includes an internal power source, such as a number of batteries, and is connected to each of the transmission coil 57 and microphone unit 58 via cables 59.

The internal assembly 52 typically includes a receiver antenna 55, a receiver/stimulator unit 53, and an intracochlear electrode assembly 54.

In operation, the microphone 58 detects sounds, such as speech and environmental sounds and converts these into an electrical signal. The electrical signal is then encoded by the speech processing electronics in the primary signal processor unit 56. The encoded output signal is then transcutaneously transmitted to the internal assembly 52 via a radio frequency (RF) link.

In recent times, the speech processor unit and the microphone unit have been combined to form a single unit that is worn behind the ear. This is referred to as a behind the ear (BTE) speech processor unit.

The speech processor unit has traditionally been worn on the body, such as by being attached to clothing, or by being supported on the ear of the recipient. The speech processor unit is relatively expensive and generally must undergo an optimization procedure following implantation of the implantable component of the system to ensure it suits the needs of the recipient. As such, most recipients only generally receive one speech processor unit.

Referring to prior art drawing FIG. 6, the BTE speech processor unit 61 is normally manufactured by moulding a main body and an inter-engageable battery carrier. This arrangement enables the batteries 62 to be readily replaced.

The BTE speech processor unit 61 is relatively expensive and must undergo an optimization procedure following implantation of the implantable assembly 52. While the operability of the signal processing aspects of the BTE speech processor unit can be varied by clinical software during the optimization procedure, usually in a clinician's practice, other aspects of operability are far more limited. This is particularly the case with external, user inter-actable features.

It is desired to provide an arrangement that improves upon earlier proposals, or at least provides a useful alternative.

SUMMARY

According to a first aspect, there is a hearing prosthesis system comprising: a first housing containing a primary signal processing unit that receives signals output by a microphone; and a plurality of second housings that are removably connectable to the first housing; wherein only one of said second housings is connectable to said first housing at any one time and further wherein at least one of said second housings has a user interface that provides control of one or more features of the operation of the primary signal processor.

In one embodiment of this aspect, one or more of said second housings can contain a power supply for at least some of the components of the prosthesis.

In another embodiment, one or more of said plurality of second housings can contain a power supply and have a user interface that provides control of one or more features of a speech processor of the hearing prosthesis system.

In yet another embodiment, one or more of said second housings can be connectable by an electrically conducting lead to a remote module housing a power supply. This second housing can be provided with a user interface on the second housing. In another embodiment, a user interface can be provided on the remote module.

In a still further embodiment, one or more of said plurality of second housings can contain signal receiver means for receiving signals from a remote module having a user interface. The signal receiver means can comprise signal receiver circuitry that receives and processes radio frequency signals output by the remote module. In this embodiment, the second housing can contain a power source. In this embodiment, the remote module can house signal transmission circuitry that send radio frequency signals to the second housing in response to adjustments made to the user interface.

In yet another embodiment, one or more of said plurality of second housings can contain signal transceiver means for receiving and sending signals from and to a remote module having a user interface. The signal transceiver means can comprise signal transceiver circuitry that receives and send radio frequency signals from and to the remote module. In this embodiment, the remote module can house signal transceiver circuitry that sends and receives radio frequency signals to and from the second housing in response to adjustments made to the user interface.

In another embodiment, one or more of said plurality of second housings can have a visual display. The visual display can comprise one or more light emitting diodes (LEDs) and/or a liquid crystal display (LCD). The visual display can provide the recipient or their carer with information about the performance of one or more aspects of the prosthesis system. In this embodiment, the second housing can contain a power source.

In yet a further embodiment, one or more of said plurality of second housings can have a user interface that is removably mounted to the second housing. In this embodiment, a plurality of different user interfaces can be connectable to said second housing. In this embodiment, only one user interface would typically be connectable to the second housing at any one time.

In a further embodiment, the remote module can have a visual display. The visual display can comprise one or more light emitting diodes (LEDs) and/or a liquid crystal display (LCD). The visual display can provide the recipient or their carer with information about the performance of one or more aspects of the prosthesis system.

According to a second aspect, there is a hearing prosthesis comprising: a first housing containing a primary signal processor that receives signals output by a microphone; and a second housing removably connectable to the first housing; wherein a user interface is provided on the second housing that provides control of one or more features of the operation of the primary signal processor.

In one embodiment of this second aspect, the hearing prosthesis can further comprise a remote module having a further user interface. The further user interface can be removably or non-removably mounted on the remote module. The further user interface of the remote module can control different features of the hearing prosthesis to that mounted on the second housing. In another embodiment, the remote module user interface can control some or all of the same features that are controllable by the user interface on the second housing. In yet another embodiment, the second housing user interface can be rendered partially or fully inoperable when a remote module as defined herein is used in conjunction with the second housing of the hearing prosthesis. In a still further embodiment, the further user interface can be mountable on either the remote module or the second housing. In this case, the recipient can, for example, choose to remove the user interface from the second housing and mount it to the remote module or vice versa. In a still further embodiment, the remote module can have a visual display. The visual display can comprise one or more light emitting diodes (LEDs) and/or a liquid crystal display (LCD). The visual display can provide the recipient or their carer with information about the performance of one or more aspects of the prosthesis.

According to a third aspect, there is a hearing prosthesis comprising: a first housing containing a primary signal processor that receives signals output by a microphone; and a remote module; wherein a user interface is provided on the remote module that provides control of one or more features of the operation of the primary signal processor.

In an embodiment, the primary signal processor is a speech processor.

According to another aspect, there is a speech processing unit for a hearing prosthesis recipient, the speech processing unit comprising: a main part configured for wearing behind an ear of the hearing prosthesis recipient, the main part including a primary signal processor for carrying out primary signal processing functions associated with the speech processing unit; and a replaceable part being removably connectable with the primary part, the replaceable part including a user interface for communication with the primary signal processor.

According to another aspect, there is a speech processing unit for a cochlear implant recipient, the speech processing unit comprising: a main part configured for wearing behind an ear of the cochlear implant recipient, the main part including a primary signal processor for carrying out primary signal processing functions associated with the speech processing unit; and a replaceable part being removably connectable with the primary part, the replaceable part including a battery compartment and user interface for communication with the primary signal processor.

In all of the aspects, the first housing containing the speech processor can be provided without any user interface such that any modification of its performance must be performed through the user interface on either the second housing and/or the remote control. In another embodiment of the aspects, one form of a user interface can be provided on the first housing. In one embodiment, this first housing user interface can control different features of the hearing prosthesis to that mounted on the second housing and/or the remote module. In another embodiment, the first housing user interface can control some or all of the same features that are controllable by the user interface on the second housing and/or the remote module. In yet another embodiment, the first housing user interface, if present, can be rendered partially or fully inoperable when a second housing and/or remote module as defined herein is used in conjunction with the first housing of the hearing prosthesis. In a still further embodiment, the first housing user interface can be removably or non-removably mounted to the first housing.

In a further embodiment, more than one type of remote module can be used in conjunction with the speech processor. The various types of remote control can vary in the type of user interface that is provided thereon and/or whether a visual display is provided. This allows a recipient and/or their carer to customize the hearing prosthesis by selecting the user interface to be used with their hearing prosthesis at any one time. The hearing prosthesis can rely on one-way or two-way wireless communication between the remote module and the speech processor. In another embodiment, signals can be transmitted from the remote module to the speech processor and/or from the speech processor to the remote module using one or more suitable cables or through radio frequency transmission system. The user interface can be removably or nonremovably mounted to the remote module.

In one embodiment, the user interface can comprise one or more push buttons or switches and/or one or more dials or rotary controls. For example, a user interface can comprise a push button that activates and/or deactivates the speech processor and/or selects the speech processor programme, a dial that allows adjustment of volume and sensitivity of the speech processor, and a further push button that allows selection of whether input to the speech processor is provided by the microphone, a telecoil or a mixture of inputs.

In one embodiment, the user interface can be enclosed within a resiliently flexible cover. The cover can be provided to protect the user interface. In addition or instead, the cover can allow more precise control of the user interface by the recipient and/or their carer.

In one embodiment, and where the hearing prosthesis comprises the second housing, the second housing can contain a power supply for at least some of the components of the prosthesis. In one embodiment, appropriate electrical connection can be made on mounting of the second housing to the first housing so that the power supply can provide power to at least the speech processor of the prosthesis.

In a further embodiment, the first housing containing the speech processor unit can be connectable to more than one type of power supply. Still further, the second housing can be connectable to the first housing in at least two orientations and/or at least two configurations.

In another embodiment, and where the hearing prosthesis comprises the remote module, the remote module can contain a power supply for at least some of the components of the prosthesis. In one embodiment, appropriate electrical connection can be made between the remote module and the speech processor so that the power supply can provide power to at least the speech processor of the prosthesis.

In one embodiment, the power supply can comprise one or more batteries, including one or more rechargeable batteries.

In one embodiment, and where the prosthesis comprises at least the first housing and the second housing, these components can be positionable on the ear of the recipient. An ear hook can be removably attached to and extend from the first housing to facilitate mounting of the external component of the prosthesis to the ear of the recipient. In another embodiment, these components can be adapted to be worn on the body, such as by being clipped to or placed in the pocket of clothing being worn by the recipient.

In one embodiment, the speech processor can receive signals output from a microphone that is mounted on or within the first housing. In another embodiment, the speech processor can receive signals from a microphone that is mounted on the remote module. Still further, the speech processor can receive signals from more than one microphone.

The speech processor can be used in conjunction with a range of different remote modules having different user interfaces thereon. This allows a recipient or their carer to customize the hearing prosthesis by selecting the user interface to be used with their hearing prosthesis at any one time.

Alternative user interface types could be provided on the remote module 32 or on different remote modules used in conjunction with the speech processor 31.

In one embodiment, and where the prosthesis comprises at least the first housing and the second housing, these components can be positionable on the recipient. An ear hook can be removably attached to and extend from the first housing to facilitate mounting of the external component of the prosthesis to the ear of the recipient. In another embodiment, these components can be adapted to be worn on the body, such as by being clipped to or placed in the pocket of clothing being worn by the recipient.

BRIEF DESCRIPTION OF THE DRAWINGS

By way of example only, embodiments are described with reference to the accompanying drawings, in which.

DETAILED DESCRIPTION

Figure 1:
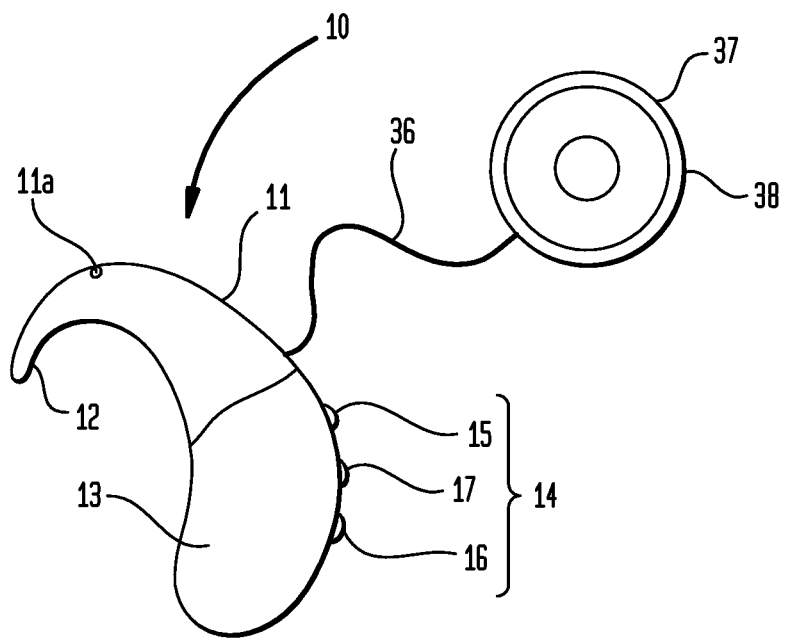
FIG. 1 is a side elevation view of an external component of a hearing prosthesis according to the present disclosure.

Referring to FIG. 1, a BTE speech processor unit 10 includes a first housing 11 (or a main part), an ear hook 12 and a second housing 13 (or replaceable part). The first and/or second housing can be formed of a metallic material, a ceramic material, a polymeric material, or some combination thereof. The first housing could be formed of a different material, or the same material, to that used for the second housing.

The BTE speech processor unit 10 is connected to a headpiece 37 via a cable 36 which extends from the first housing 11.

The first housing 11 includes a primary signal processing electronics for operating the BTE speech processor unit 10. In this example, a microphone 11a is mounted on the first housing 11. However, the microphone can be positioned elsewhere, such as on the headpiece 37, on the second housing 13, or on the clothing of the recipient.

The component 10 can be worn on the ear of a recipient of the implant system. The component 10 has a first housing 11 containing speech processor circuitry that receives signals output by a microphone. Extending forwardly from the first housing 11 is an ear hook 12. The depicted ear hook 2 is removably attached to the first housing 11. The microphone can be mounted on the housing 11 or be positioned at another location.

The headpiece 37 comprises an antenna coil 38 that is capable of transmitting signals to a complementary antenna implanted within the recipient. In addition, the antenna coil 38 is capable of receiving signals transmitted from the implanted antenna.

The antenna coil 38 surrounds a magnet 39 that is attracted to a complementary magnet implanted within the recipient The magnetic attraction serves to retain the antenna coil 38, during use, in the desired position on the head of the recipient.

The BTE speech processor unit 10 further comprises a second housing 13 that is removably connectable to the first housing 11. It is envisaged that the second housing 13 is normally replaceable by the recipient.

The second housing 13 includes a user interface panel 14 having two push buttons 15, 16 and a dial 17. Push button 15 is used to activate and deactivate the speech processor within the first housing 11 and is also used to select the speech processor programme being performed by the speech processor. The dial 17 allows adjustment of the volume and sensitivity of the speech processor while the push button 16 allows the recipient or their carer to select whether the input to the speech processor is provided by the microphone, a telecoil or a mixture of inputs. The user interface panel 14 is either removably or non-removably mounted to the second housing 13.

The present inventors have realised that providing for replaceability or interchangeability of the user interface can provide significant recipient benefits, compared with the manufacturing costs and total purchasing costs for an external component assembly of a hearing prosthesis. For example, it may be desired to provide larger push buttons for the elderly while children and infants may require more simplified interlockable controls. Similarly, an experienced user may require a more complex interface and/or greater flexibility with the internal workings of the speech processor.

Another advantage includes that the recipient can choose the user interface that suits them and/or their lifestyle. They also have the option of being able to delay a final decision as to which user interface they wish to use until after the purchase of the speech processor unit. If desired, they also have the option of changing the user interface of their system without the need to purchase a new speech processor unit The system also has the advantage that the user is able to upgrade their user interface if and when desired. An upgrade may be made because a new type of user interface has been made available and/or because the user interface has failed and so needs to be replaced. The user interface being actuatable is vulnerable to damage and this ability to be able to replace the user interface without having necessarily to replace the speech processor unit is an advantage of the present system.

A further advantage of the BTE speech processor unit is that the parts which are most vulnerable to damage and/or that are less expensive can be easily replaced.

Figure 2:
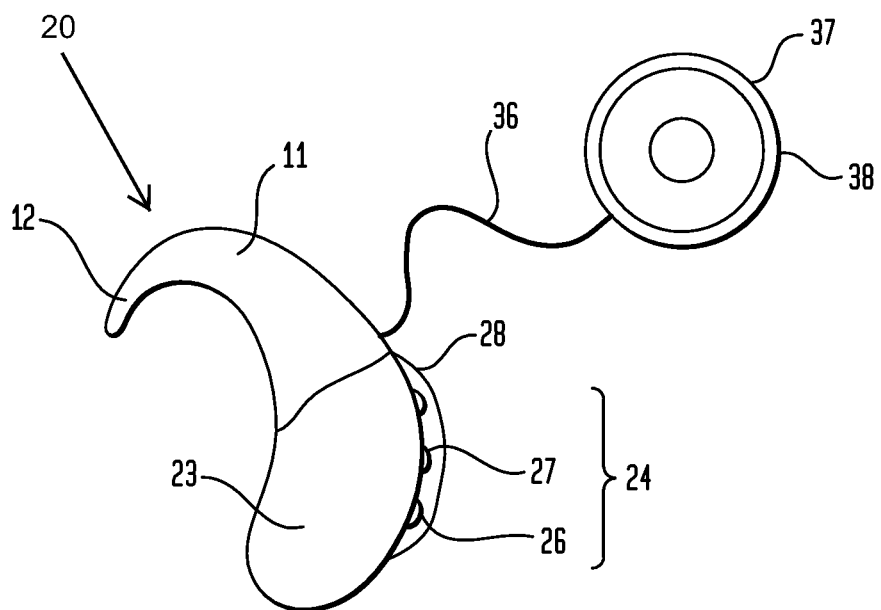
FIG. 2 is a side elevation view of another external component of a hearing prosthesis according to the present disclosure.

Turning now to FIG. 2, there is depicted a BTE speech processing unit 20 having an alternative user interface panel 24. As with the user interface panel described in relation to FIG. 1, the interface panel 24 of FIG. 2 can be removably or non-removably mounted to the second housing 23.

The user interface panel 24 includes two tactile position controls 25, 26 that, through their position, provide feedback to the recipient and/or their carer as to the setting of that control. Both tactile position controls 25, 26 comprise a switch that is movable between at least three settings. Switch 25 is a three-position switch that allows a recipient and/or their carer to select which speech programme is to be used. Dial 27 allows adjustment of the volume and sensitivity of the speech processor. Switch 26 allows a recipient and/or their carer to set whether the speech processor is receiving input from the microphone, a telecoil, or a mix of such inputs. The switch 26 also allows the recipient and/or their carer to adjust the operation of the speech processor such that it can detect relatively softer sounds, such as whispers.

It will be noted that the system 40 could also incorporate the housing 23 as is depicted by FIG. 2 having a tactile user interface 24.

In FIG. 2, the user interface 24 is enclosed within a resiliently flexible cover 28. The cover 28 protects the user interface 24 but also allows more precise control of the user interface 24 by the recipient and/or their carer.

In the arrangements shown in FIGS. 1 and 2, the first housing 11 for the speech processor is provided without a user interface. Therefore, any modification of its performance must be performed through the user interface on the second housing (13 or 23).

As shown in FIGS. 1 and 2, more than one type of second housing can be removably mountable to the first housing 11. The various types of second housing can vary in the type of user interface panel that is provided thereon, This allows a recipient and/or their carer to customise the hearing prosthesis by selecting the user interface to be used with their hearing prosthesis at any one time.

The first housing containing the speech processor unit can be connectable to more than one type of power supply. In the examples of FIGS. 1 and 2, the second housing (13 or 23) contains a power supply for powering the componentry of the prosthesis. On mounting of the second housing (13 or 23) to the first housing (11), the power supply is able to provide power through an electrical connection to the speech processor. The power supply within the second housing can comprise one or more rechargeable batteries.

Figure 3:
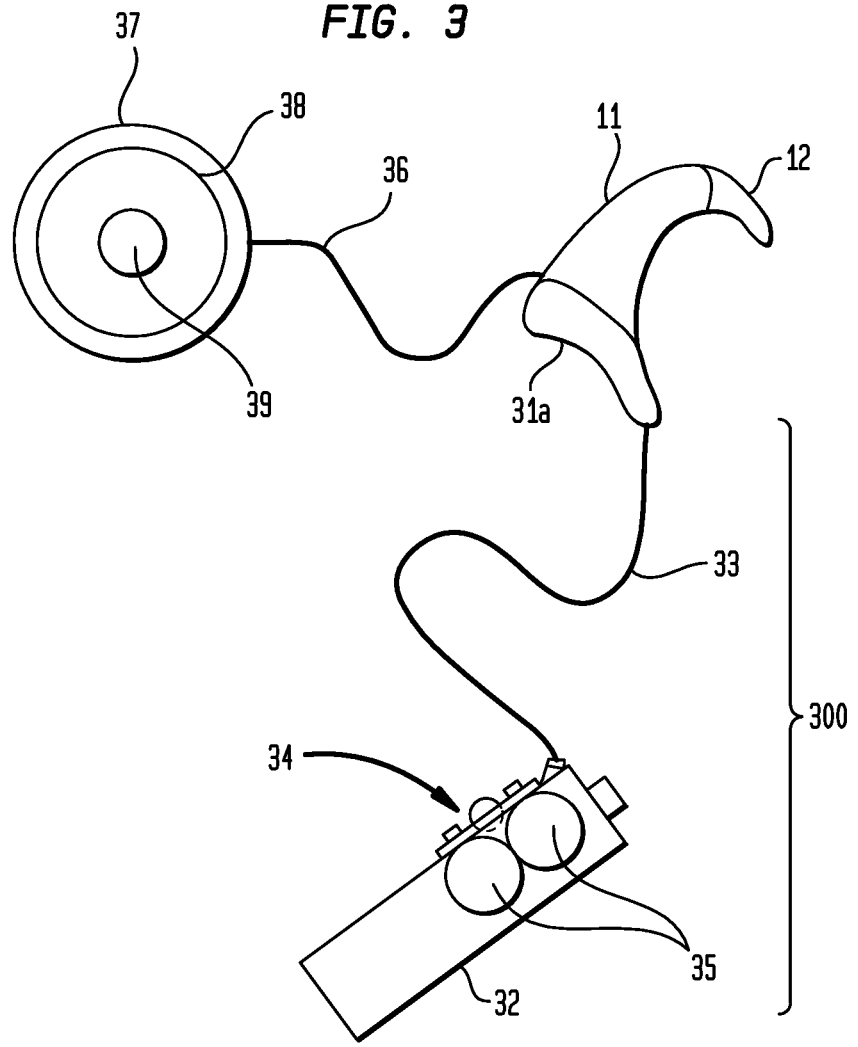
FIG. 3 is a view of another external component of a hearing prosthesis according to the present disclosure.

Referring now to FIG. 3, there is shown the first housing 11 and an ear hook 12 as earlier described in relation to FIG. 1. However in comparison with the arrangement described in relation to FIG. 1, the second housing 13 is replaced by assembly 300. Assembly 300 includes a connector unit 31a and a remote module 32, connected via cable 33.

The first housing 11 relies on cable 33 to provide data and power transfer between the remote module 32 and a connector unit 31a that is removably connectable with the speech processor 31. However, it will be appreciated that wireless transmission can be utilised to transfer data and control signals between the remote module 32 and the speech processor and/or vice versa.

The remote module 32 includes a user interface panel 34, which is optionally removable/replaceable from the connector unit 31a. In the case of a removable/replaceable interface panel 34, this allows a recipient and/or their carer to further customise the hearing prosthesis by selecting the user interface to be used with their hearing prosthesis at any one time.

The user interface panel 34 includes two push-button switches and a dial similar to that of user interface panel 14 earlier described in relation to FIG. 1.

In the example shown in FIG. 3, the remote module 32 also houses a power supply for at least some of the componentry of the external component 30 and particularly the speech processor. The power supply can comprise two rechargeable batteries 35.

The remote module 32 can be worn on the body of the recipient, such as by being clipped to or placed in the pocket of clothing of the recipient.

Figure 4:
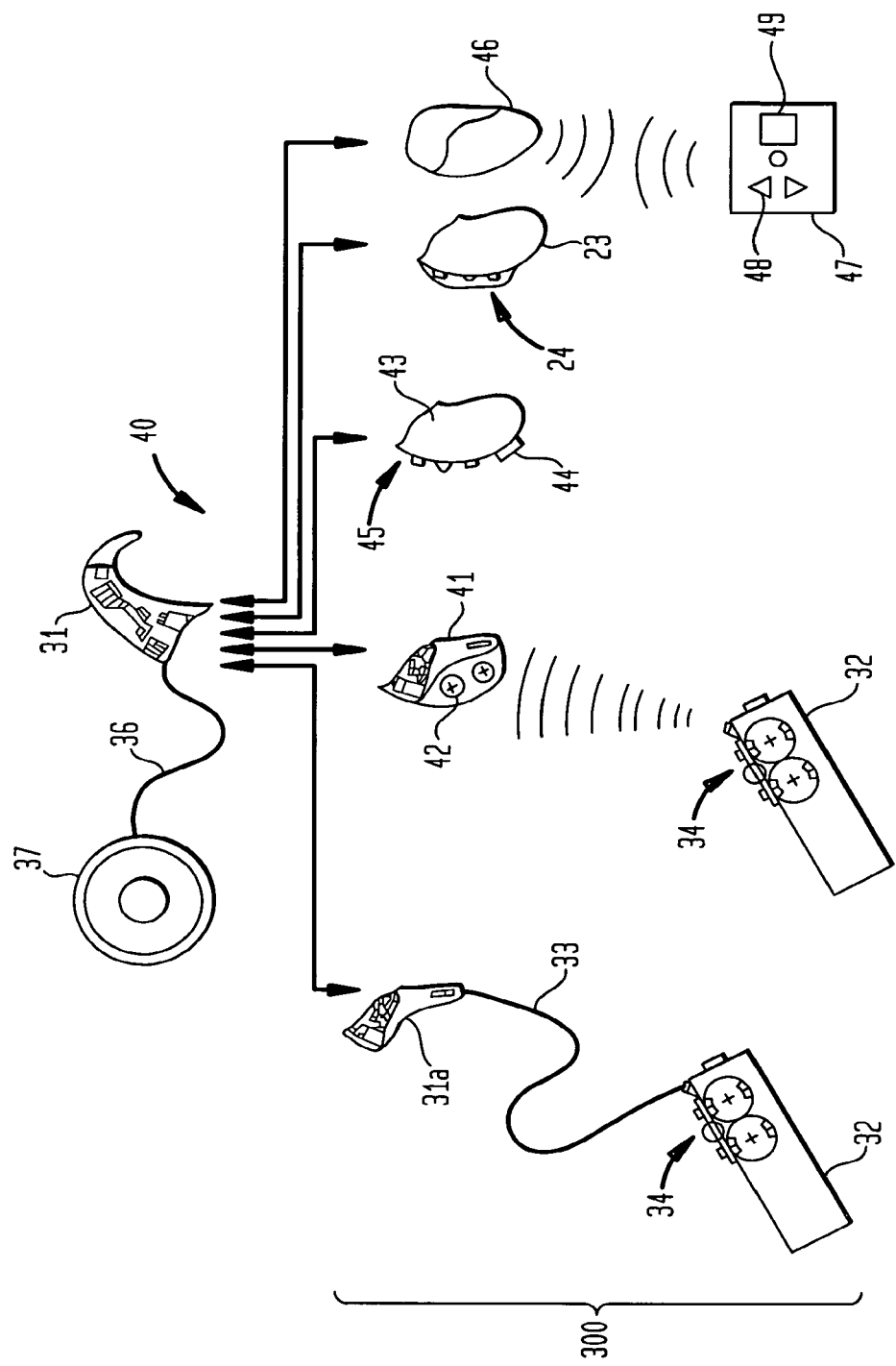
FIG. 4 is a schematic view of a hearing prosthesis system according to the present disclosure.
Figure 5:
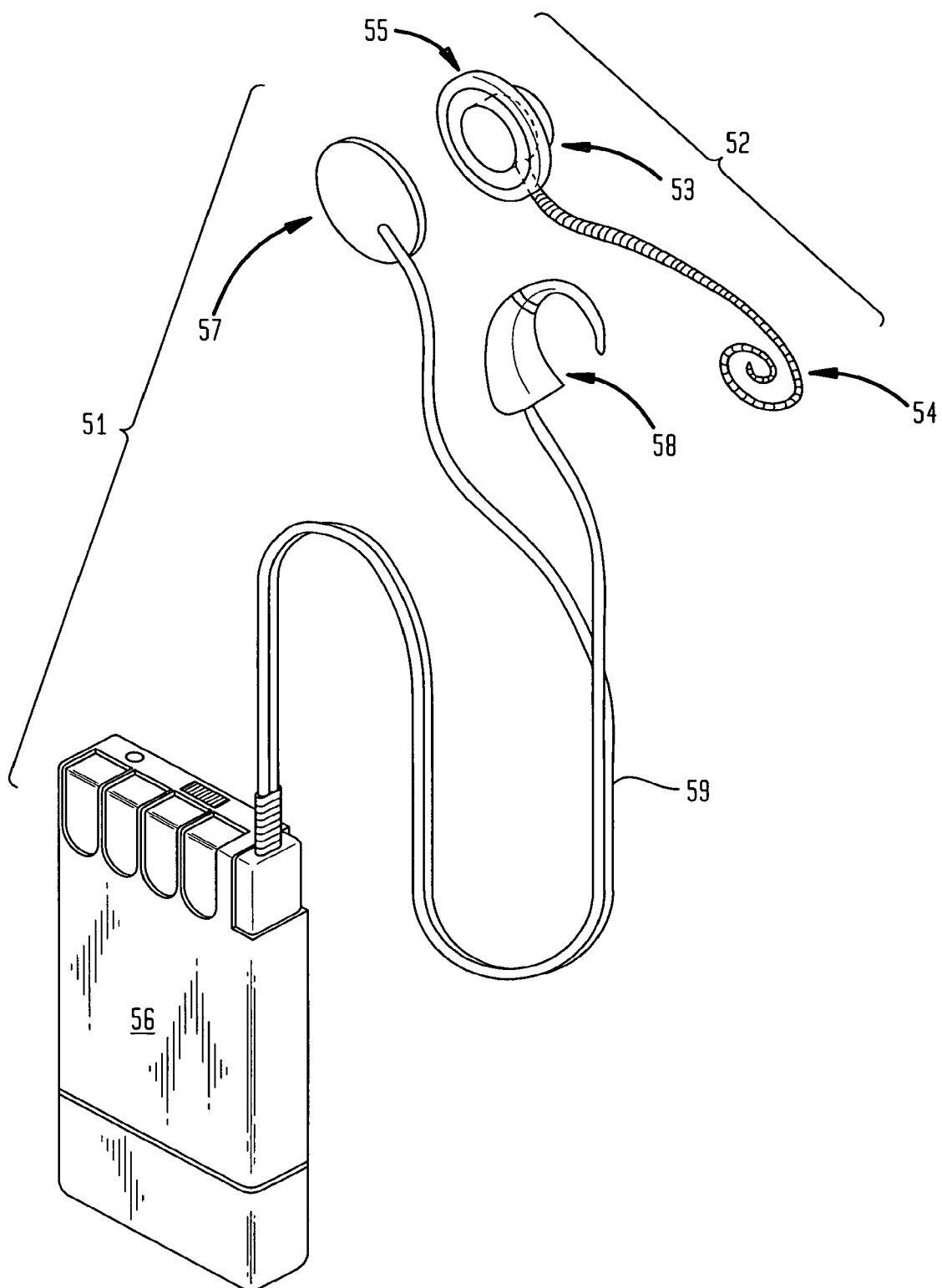
FIG. 5 is an example of a prior art external assembly.
Figure 6:
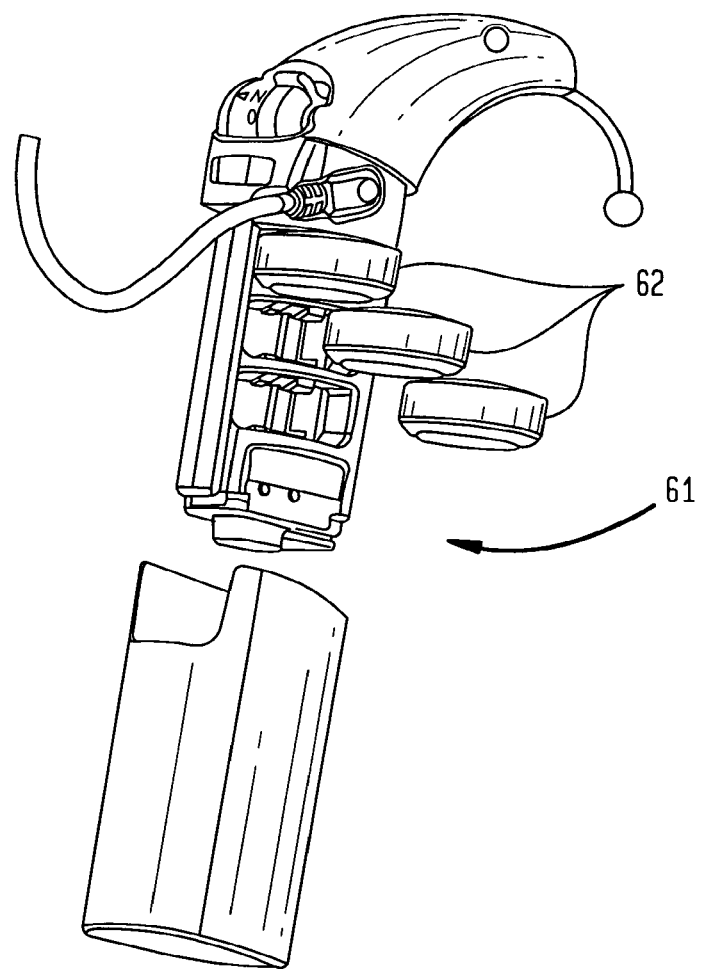
FIG. 6 is another example of a prior art external assembly.

A system of interchangeable parts will now be described with reference to FIG. 4.

The first housing 11 can be provided as part of a hearing prosthesis system 40 which can provide several interchangeable configurations. Hence the recipient or their carer is provided with a number of options as to what may be connected to the speech processor 31 housing at any one time.

The system 40 includes an option to connect a second housing 41 that includes a power supply 42 and radio frequency (RF) signal receiver circuitry that receives and processes RF signals output by the remote module 32. In this arrangement the remote module 32 incorporates RF signal transmission circuitry for transmitting signals to the housing 41 in response to adjustments made to the user interface 34 on the remote module 32.

The system 40 can also include an option to connect a second housing 43 that includes a power supply, a visual display device 44 and user interface 45. The exemplary display device 44 is a liquid crystal display, however, other suitable displays are envisaged. The liquid crystal display 44 provides feedback to the recipient or their carer as to the performance of the system 40.

The system 40 can also include an option to connect a second housing 46 that includes a power supply and circuitry that not only receives and processes RF signals but also can transmit signals back to a remote module 47. In this case, the remote module 47 as well as housing a power source has a user interface 48 and a liquid crystal display (LCD) 49 for providing feedback to the recipient or their carer as to the performance of the system 40.

Optionally, the first housing user interface can control some or all of the same features that are controllable by the user interface on the second housing 23 and/or the remote module 32. The first housing user interface, if present can be rendered partially or fully inoperable when a second housing' 23 and/or remote module 32 as defined herein is used in conjunction with the first housing of the hearing prosthesis. The first housing user interface can be removably or non-removably mounted to the first housing.

It is noted that remote module 31 could, also be used in conjunction with the components 10 and 20 depicted in. FIGS. 1 and 2, respectively.

The user interface of the second housing 23 and/or the remote module 32 can be selected from a range of types of user interfaces that are available for use by the recipient of the hearing prosthesis or the recipient's carer. For example, the user interface of the second housing 23 can be the same or different from that available on a remote module 32. Where a user interface is provided on the first housing, the user interface of the second housing and/or the remote module can be different from that provided on the first housing.

In alternative configurations, one form of a user interface can be provided on the first housing 11 to control different features of the hearing prosthesis than that of the features controlled by the user interface panel of the second housing 23 and/or the remote module 32.

It will be appreciated by persons skilled in the art that numerous variations and/or modifications may be made to the teachings shown in the specific embodiments without departing from the scope of the teachings broadly described. The present embodiments are, therefore, to be considered in all respects as illustrative and not restrictive.

Throughout this specification the word "comprise", or variations such as "comprises" or "comprising", will be understood to imply the inclusion of a stated element integer or step, or group of elements, integers or steps, but not the exclusion of any other element, integer or step, or group of elements, integers or steps.

It will be appreciated by persons skilled in the art that numerous variations and/or modifications may be made to the specific embodiments without departing from the spirit or scope of the invention as broadly described. The present embodiments are, therefore, to be considered in all respects as illustrative and not restrictive.

What is claimed is:

1. A system, comprising:
a first housing containing a speech processor that receives signals output by a microphone of the system;
a second housing removably connectable to the first housing at a bottom of the first housing, the bottom being at a first end of the first housing that is a wider end relative to a second end of the first housing opposite the first end; and
a first device removably connectable to the first housing when the second housing is disconnected from the first housing, wherein
the first housing is part of a behind-the-ear (BTE) device,
the second housing is part of a second device, and
the system is a cochlear implant hearing prosthesis system.

2. The system of claim 1, wherein:
the second device is different in physical size from the first device.

3. The system of claim 2, wherein:
a user interface is on the first housing.

4. The system of claim 3, wherein:
the first device includes a first power supply, which first power supply powers the speech processor when the first device is removably connected to the first housing; and
the second device includes a second power supply, which second power supply powers the speech processor when the second device is removably connected to the first housing.

5. The system of claim 4, wherein:
the second power supply is different in physical size than the first power supply.

6. The system of claim 5, wherein:
the first housing is configured to receive a third housing different in form from the second housing, when the second housing is removed, at the bottom of the first housing, the third housing being part of the first device.

7. The system of claim 6, wherein:
the first device is different in shape from the second device.

8. The system of claim 7, wherein:
the first power supply is a rechargeable power supply; and
the second power supply is a non-rechargeable power supply.

9. The system of claim 4, wherein:
the first power supply is a rechargeable power supply, and
the second power supply is a non-rechargeable power supply.

10. The system of claim 9, wherein:
the second housing includes structure that extends into the first housing when the second housing is removably connected to the first housing.

11. The system of claim 4, wherein:
the first housing and the second housing, when the second housing is coupled to the first housing, establish a body-worn external component of a cochlear implant hearing prosthesis of the cochlear implant hearing prosthesis system;
the system further comprises a remote module that includes RF signal circuitry; and
the system is configured so that wireless transmission can be utilized to transfer data from the body-worn external component to the remote module.

12. The system of claim 4, wherein:
the first housing and the second housing, when the second housing is coupled to the first housing, establish a body-worn external component of a cochlear implant hearing prosthesis of the cochlear implant hearing prosthesis system;
the system further comprises a remote module that includes RF signal transmission circuitry that is configured to output RF signals so that wireless transmission can be utilized to transfer data and control signals between the remote module and the body-worn external component of the cochlear implant hearing prosthesis;
the remote module can control at least some features of the cochlear implant hearing prosthesis system;
the user interface can control at least some features of the cochlear implant hearing prosthesis system; and
one or more of the features controlled by the remote module are the same as those controlled by the user interface.

13. The system of claim 1, wherein:
the second device includes a power supply; and
the second housing and the power supply collectively establish a means for providing power to the speech processor when the second device is removably connected to the first housing.

14. The system of claim 1, wherein:
the second housing includes structure that extends into the first housing when the second housing is removably connected to the first housing.

15. The system of claim 1, wherein:
the first device is a modular means for providing power to the speech processor when the first device is removably connected to the first housing, the modular means being rechargeable; and
the second housing includes a battery compartment.

16. The system of claim 1, wherein:
the first device includes first electronics components, the electronics components of the first device consisting of a first power supply that powers the speech processor when the first device is connected to the first housing; and
the second device includes second electronics components, the electronics components of the second device consisting of a second power supply that powers the speech processor when the second housing is connected to the first housing.

17. The system of claim 16, wherein:
the second device is different in physical size from the first device; and
a user interface is on the first housing.

18. The system of claim 17, wherein:
the second power supply is different in physical size than the first power supply.

19. The system of claim 18, wherein:
the first device has different performance characteristics than the second device;
the first housing is configured to receive a third housing different in form from the second housing, when the second housing is removed, at the bottom of the first housing, the third housing being part of the first device; and
the first device is different in shape from the second device.

20. The system of claim 19, wherein:
the first power supply is a rechargeable power supply, and
the second power supply is a non-rechargeable power supply.

21. The system of claim 20, wherein:
the second housing includes structure that extends into the first housing when the second housing is removably connected to the first housing.

22. The system of claim 20, wherein:
the first housing and the second housing, when the second housing is coupled to the first housing, establishes a body-worn external component of a cochlear implant hearing prosthesis of the cochlear implant hearing prosthesis system;
the system further comprises a remote module that includes RF signal circuitry; and
the system is configured so that wireless transmission can be utilized to transfer data from the body-worn external component to the remote module;
the remote module can control at least some features of the cochlear implant hearing prosthesis system;
the user interface can control at least some features of the cochlear implant hearing prosthesis system;
one or more of the features controlled by the remote module are the same as those controlled by the user interface; and
the remote module includes a microphone mounted on the remote module, and the signal processor receives signals from the microphone mounted on the remote module.

23. The system of claim 20, wherein:
the first housing and the second housing, when the second housing is coupled to the first housing, establishes a body-worn external component of a cochlear implant hearing prosthesis of the cochlear implant hearing prosthesis system; and
the system further comprises a remote module that includes RF signal transmission circuitry that is configured to output RF signals so that wireless transmission can be utilized to transfer data and control signals between the remote module and the body-worn external component.

24. The system of claim 5, wherein:
the first device has different performance characteristics than the second device.

25. The system of claim 7, wherein:
the first power supply includes a plurality of batteries.

26. The system of claim 25, wherein:
the second power supply is within the second housing and is one battery.

27. The system of claim 7, wherein:
the second housing includes structure that extends into the first housing when the second housing is removably connected to the first housing.

28. The system of claim 7, wherein:
the first housing and the second housing, when the second housing is coupled to the first housing, establishes a body-worn external component of a cochlear implant hearing prosthesis of the cochlear implant hearing prosthesis system;
the system further comprises a remote module that includes RF signal circuitry; and
the system is configured so that wireless transmission can be utilized to transfer data from the body-worn external component to the remote module.

29. The system of claim 7, wherein:
the first housing and the second housing, when the second housing is coupled to the first housing, establishes a body-worn external component of a cochlear implant hearing prosthesis of the cochlear implant hearing prosthesis system; and
the system further comprises a remote module that includes RF signal transmission circuitry that is configured to output RF signals so that wireless transmission can be utilized to transfer data and control signals between the remote module and the body-worn external component.

30. The system of claim 7, wherein:
the system further comprises a remote module that includes RF signal transmission circuitry that is configured to output RF signals, wherein
the first housing and the second housing, when the second housing is coupled to the first housing, establishes a body-worn external component of a cochlear implant hearing prosthesis of the cochlear implant hearing prosthesis system;
the remote module can control at least some features of the cochlear implant hearing prosthesis system;
the user interface can control at least some features of the cochlear implant hearing prosthesis system; and one or more of the features controlled by the remote module are the same as those controlled by the user interface.

\* \* \* \* \*